United States Patent [19]

Kempe et al.

[11] Patent Number: 5,099,735
[45] Date of Patent: Mar. 31, 1992

[54] VERSATILE KNIFE HOLDER FOR MICROTOME KNIVES

[75] Inventors: Manfred Kempe, Neckargmuend; Georg Herrmann, Walldorf; Manfred Biehl, Meckesheim, all of Fed. Rep. of Germany

[73] Assignee: Leica Instruments GmbH, Heidelberg, Fed. Rep. of Germany

[21] Appl. No.: 627,717

[22] Filed: Dec. 14, 1990

[30] Foreign Application Priority Data

Dec. 15, 1989 [DE] Fed. Rep. of Germany ... 8914782[U]

[51] Int. Cl.⁵ .......................... B26D 1/02; G01N 1/06
[52] U.S. Cl. ...................................... 83/700; 83/856; 83/915.5; 83/DIG. 1
[58] Field of Search ...................... 83/700, 856, 915.5, 83/954, DIG. 1

[56] References Cited

U.S. PATENT DOCUMENTS

| 3,552,733 | 1/1971 | Pickett | 269/216 |
| 4,690,023 | 9/1987 | Berleth et al. | 83/700 |
| 4,700,600 | 10/1987 | Pickett | 83/165 |

FOREIGN PATENT DOCUMENTS 3616659  8/1987  Fed. Rep. of Germany .

Primary Examiner—Frank T. Yost
Assistant Examiner—John M. Husar
Attorney, Agent, or Firm—Bean, Kauffman & Spencer

[57] ABSTRACT

A microtome knife holder comprises a support element provided on the base connected to a microtome and at least one jaw for clamping the knife that is adjustable along a rail of the support element in the same direction as the cutting edge of the knife and releasably securable on said supporting element at a desired location. The guide means if formed of a prism rail of substantially dovetailed profile, a slotted foot portion of the holder is formed with a matching complementary profile and compressible by means of at least one screw engaging around said prism rail. Different holders, usually for different types of knives, can easily be slid on or off the rail. A quick release clamp and edge guard are also disclosed.

17 Claims, 6 Drawing Sheets

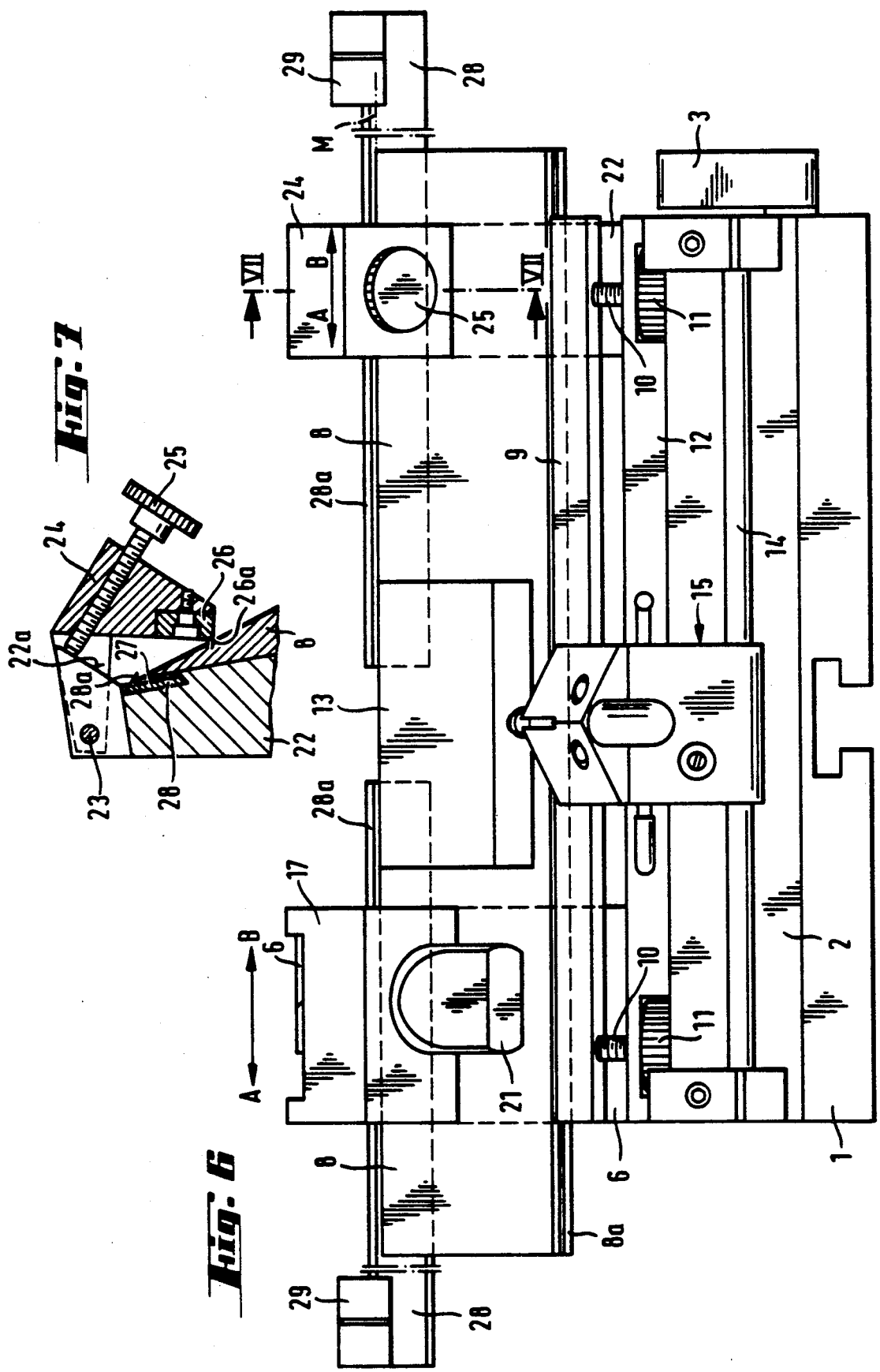

VERSATILE KNIFE HOLDER FOR MICROTOME KNIVES

BACKGROUND OF THE INVENTION

The present invention relates to microtome knife holders and more particularly to improvements in the versatility of such holders, the accessibility of replaceable knives and the inter-changeability of holders for different types of knives.

One advantage of the present invention is provided by a dove-tailed rail secured to a holder base which is rotatable on an axis coincident with the cutting edge of a plurality of knives each held by a different type of holder. An individual holder to hold a disposable, Ralph, glass or replaceable knife is mounted by sliding the selected holder on to the dove-tailed rail and then clamping it in the desired position. Prior art devices required that the entire base and be replaced as taught by DE-P 34 13 278.3.

The invention also relates to a clamping device for the cutting knife of a microtome comprising a support element provided on the microtome and at least one clamping jaw adjustable along a guide means of the support element longitudinally of the cutting blade of the knife and arrestable on said supporting means.

A clamping device of this type is disclosed in DE-PS 36 16 659. The clamping jaws are guided in a longitudinal groove and the support element comprises at least one longitudinal slot through which a fastening means extends for securing the clamping jaws to the support element.

The invention is based on the object of improving a clamping device of the above-mentioned kind such that different clamping jaws can be easily and quickly combined with the support element, exchanged with each other in modular fashion and are reliably secured to the support element.

According to the invention, this object is solved in that the guide means is formed of a prism rail having a substantially dovetailed profile, a slotted foot portion of the clamping jaw formed with a matching complementary profile and compressible by means of at least one screw engaging around said prism rail.

A particularly stable clamping of the knife is accomplished if, in accordance with one embodiment of the invention, the cutting knife is clamped-in by means of two clamping jaws which are provided substantially symmetrical on both sides of the area of cut. It is also desireable that the space between the clamps be adjustable in order that maximum stability can be achieved. Depending on whether it is more important in the individual cutting operation to provide free accessibility of the area of cut or a high resistance to moment and a high resistance of the knife to bending in order to enable a smooth, vibration-free cutting operation, the distance between the points where the knife is clamped-in can be adjusted without problem in accordance with the requirements of the individual applications.

If it is desired to provide free accessibility to the cutting knife is as freely accessible as possible, according to another embodiment of the invention, the cutting knife is clamped-in by means of a single main clamping jaw which is disposed laterally of the area of cut. In order to provide greater stability without substantial loss of free accessibility to the cutting knife, the free end of the cutting knife clamped-in the main clamping jaw can in addition be clamped-in a supplementary clamping jaw which is smaller than the main clamping jaw and is easier to be secured.

In any case, the back of the cutting knife advantageously rests on a supporting rail which is vertically adjustable by means of adjustment screws to provide a clamping mechanism for the knife which can be easily adapted to different commercially available knives of different shapes and which allows the cutting blade of the knife to be adjusted to the pivot axis of the rotatable base.

According to the invention, an insertion of the knife from the front and a quick exchange and reliable clamping-in of a replaceable knife is enabled in that a clamping latch is pivotally mounted on the top end of the clamping jaw, which latch can be swung down to contact the side of the knife resting with its back on the supporting rail, said clamping latch being adapted to be pressed against the knife by means of a tensioning screw screwed through the clamping latch, the screw end being supported on a support surface of the clamping jaw.

The clamping means of the invention allows the cutting knife to be inserted from the front (a direction normal to the orienting surface) so that it no longer needs to be inserted from the top or side, which often results in damage being caused to the cutting blade.

According to the invention, the cutting knife is reliably retained in that a narrow edge of the clamping latch extending in parallel to the cutting edge rests on the cutting knife. Said edge is brought in backlash-free line contact with the knife surface and the knife is reliably pressed against its support surface in particular in that, in accordance with further preferable features of the invention, the edge resting on the cutting knife is provided on a floating member, pivotally mounted to the clamping latch and the edge includes a central recess in its longitudinal extension.

According to the invention, the tension screw is provided on the pivotal clamping latch and serves to tighten the exchangeable cutting knife with an automatic adaptation to different knife thicknesses so that the usual commercial cutting knives differing highly as regards thickness and cutting angle can be quickly and reliably clamped-in by a one-hand operation. To impart the full clamping force to the to turn the tension screw by approximately 180°. Unlike in known knife holders, only one single control member is required in order to clamp-in the knife and to enable an adjustment to a specific knife thickness.

The floating member facilitates the adjustment to different cutting angles, reduces the surface pressure encountered at the point of contact with the knife and ensures a parallel alignment between the knife and the knife support. As a result, new and old knives can be used without restriction and the so-called "dragging cut" which occurs in case of non-parallel adjustment is eliminated.

According to a further advantageous feature of the invention, the clamping jaw is provided with a bevel to further facilitate the manipulation of the quick-action clamping means, said bevel surface being so located in the path travelled by the end of the tension screw when the clamping latch is swung towards the knife that, during the pivotal movement of the clamping latch, it axially displaces the screw end out of the area of the support surface cooperating with the screw end and releases it again at the end of the pivotal movement, a return spring biases the clamping latch against this axial movement.

In this way it is possible, by a mere axial displacement, to remove the clamping latch from the knife flank, i.e., to open the clamping latch, so that the knife can be exchanged or longitudinally shifted to expose another area of cut. By exerting a slight pressure on the tensioning screw, the clamping latch is then automatically closed again via the inclination of the bevel surface.

According to the invention, an exchange or shift of the cutting knife is further facilitated in that a spring is provided which holds the clamping latch in a position in which it is swung away from the knife which spring retains the clamping latch in its opened position after it has been unlocked. A configuration which is particularly easy to manufacture is provided in that a spring is provided on the axis of the clamping latch which tends to urge the clamping latch both in axial direction and to lift it away from the cutting knife in pivotal direction.

Finally, according to the invention, the abutment surface for the cutting knife includes in proximity to the cutting blade a prism guide of substantially dovetailed shape for a knife guard which is movable longitudinally. Appropriately, the guard is formed with the dovetailed profile corresponding to the recess and includes at its upper edge a lip projecting around the cutting blade to protect the cutting blade and, furthermore, to prevent the knife from inadvertently moving away from the knife orienting surface when the clamping latch assumes its opened position. Furthermore, a handle is provided in proximity to one end of the guard.

In this way, a guard is provided which is easy to manufacture and whose guide means is disposed fully below or flush with the knife support surface so that it does not impair in any way the insertion or exchange of the cutting knife and reliably protects the knife also against stronger outer influences and can be easily and quickly removed from the cutting edge at the beginning of the cutting operation. Furthermore, the guard prevents the cutting knife from moving away from its support surface when the clamping means assumes its opened position.

The clamping device of the invention is furthermore advantageous in that it can be easily disassembled so that the component parts can be disinfected individually in an easy fashion.

BRIEF DESCRIPTION OF THE DRAWINGS

The knife holder of the invention will now be described in detail with reference to the attached drawings wherein:

FIG. 6 shows the same view as FIG. 5, the cutting knife being clamped-in on either side of the area of cut and being retained by a main clamping jaw and a supplementary clamping jaw; and FIG. 7 shows a section through the clamping means of the supplementary clamping jaw along line VII—VII of FIG. 6.

DESCRIPTION OF THE PREFERRED EMBODIMENTS

Figure 1:
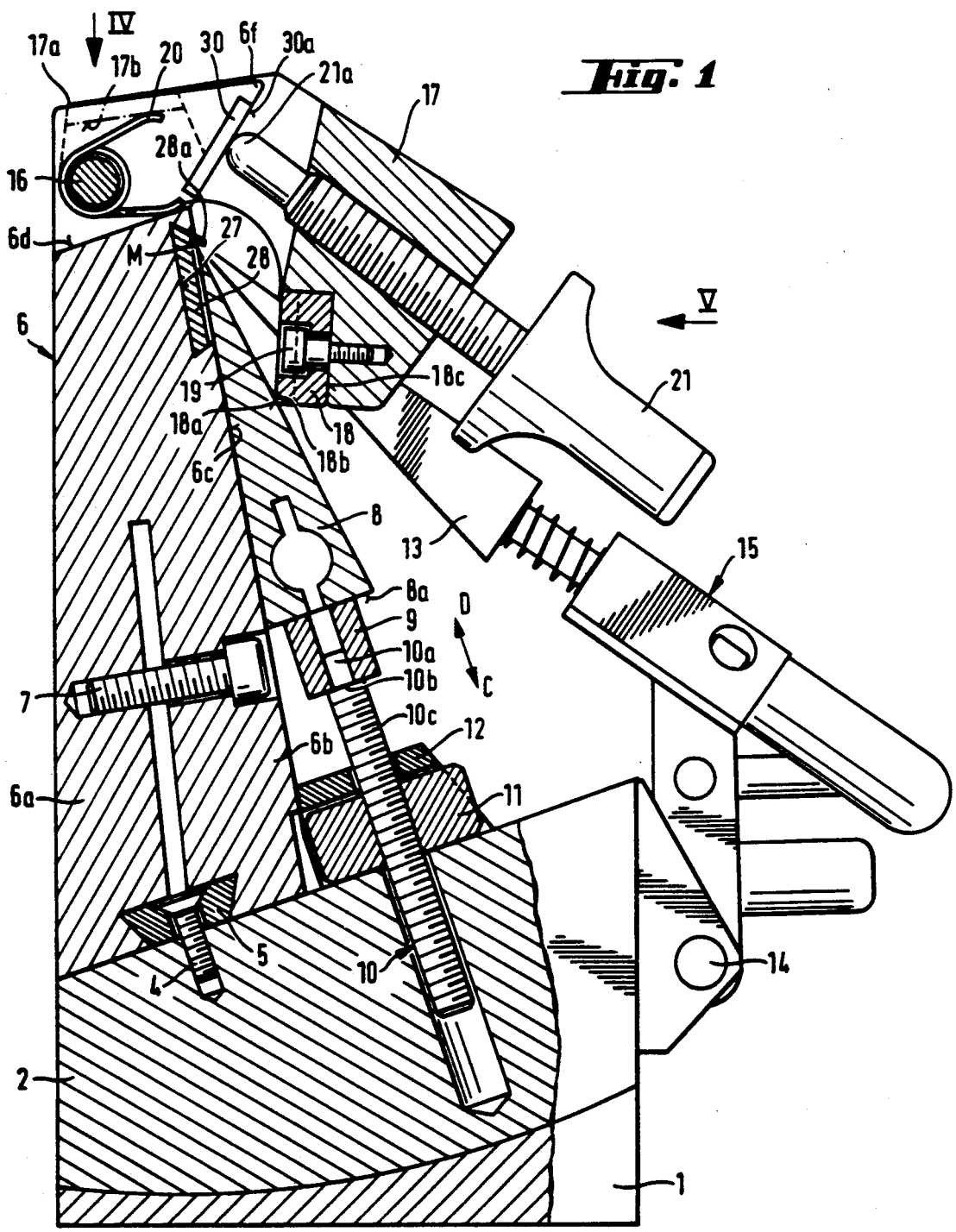
FIG. 1 shows a section through the clamping device of the invention along line I—I of FIG. 5.
Figure 5:
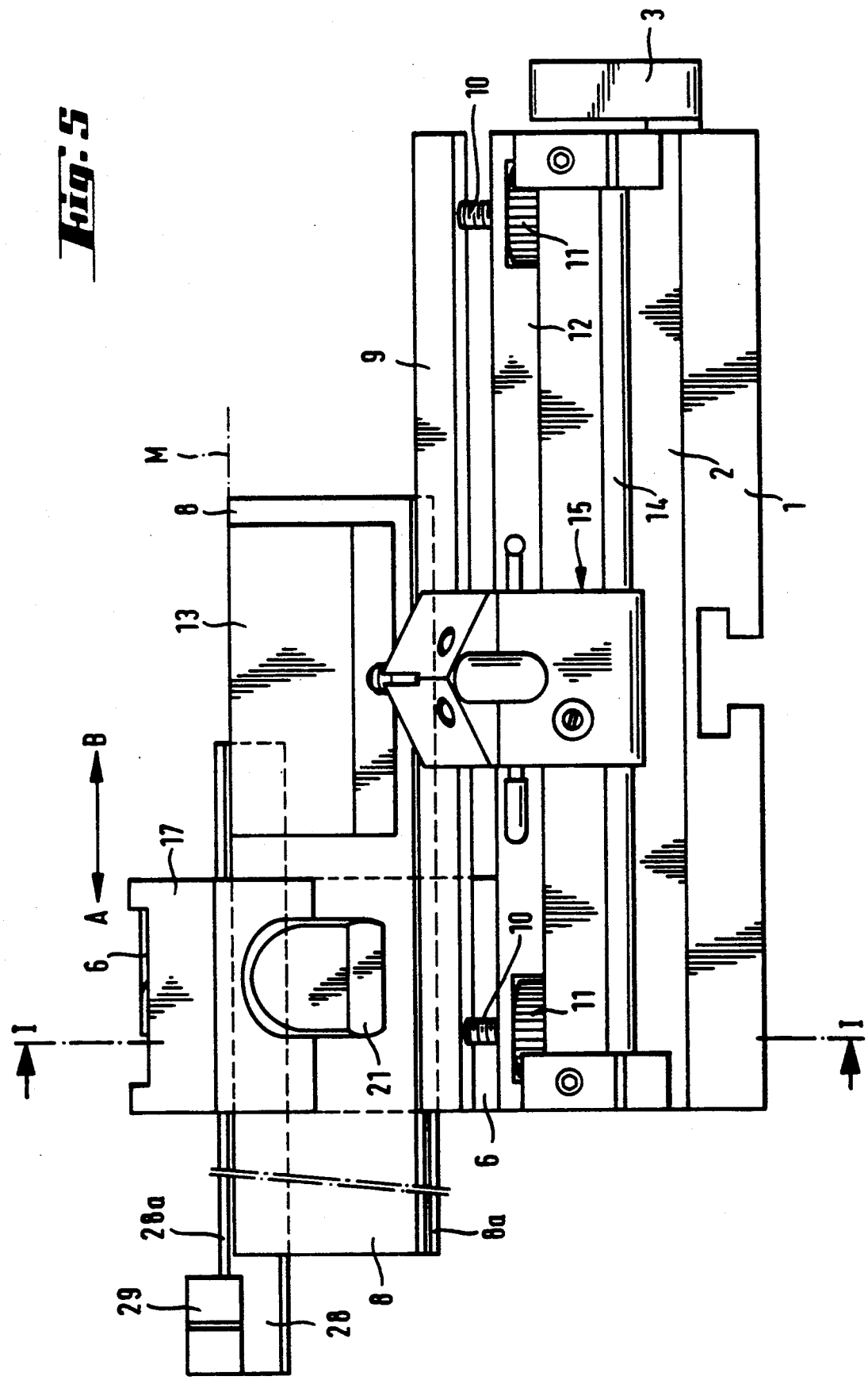
FIG. 5 shows a view of the clamping device of the invention along arrow V of FIG. 1 with an asymmetrically installed clamping jaw and unilaterally clamped-in cutting blade.

According to FIGS. 1 and 5, base member 2 is slidably mounted on bottom member 1 for rotational movement about axis M. The rotation of base member 2, which is described in detail in German Utility Model G 84 11 024.4 and will not be dealt with in more detail here, serves in known manner to set a specific cutting angle of knife 8. Operating lever 3 laterally provided on the clamping device serves to fix the selected cutting angle (FIGS. 5 and 6).

Rail 5 having a dovetailed profile is fixed to base member 2 by means of screws 4. Jaw 6 slidably engages rail 5, and is movable along said rail 5 in the directions indicated by arrows A–B. Jaw 6 has slotted foot portions 6a, 6b whose inner profile matches the dovetailed profile of rail 5. To hold jaw 6 in a selected position along rail 5, slotted foot portions 6a, 6b is capable of being pressed together by screw 7. When screw 7 is tightened, jaw 6 is connected to base member 2 without any play due to the dovetailed profiles engaging each other.

Wedge-shaped knife 8 rests against surface 6c of jaw 6, the rear portion 8a of knife 8 is supported on vertically adjustable rail 9. Rail 9 is vertically adjusted by bolts 10 on the underside of rail 9. Bolts 10 are secured against rotation by head portions 10a of diminishing cross-section forming a key-type head which engages into complementary recesses in rail 9, the latter being supported on shoulder 10b of bolts 10. Knurled nuts 11 are screwed on thread 10c of bolts 10. Nuts 11 are retained between supporting plate 12 and base member 2 to allow rotation of knurled nut 11, bolt 10, and thus rail 9, can be shifted in the directions indicated by arrows C–D. In this way, conventional knives of different shapes and sizes resting on abutment surface 6c can be shifted and adjusted such that the cutting edge of the knife coincides with axis M of rotation of base member 2.

Carrier means 15 supports anti-roll plate 13 and is pivotally mounted by shaft 14 of base member 2. Anti-roll plate 13 rests in a known fashion on knife 8. Details of this section straightening or anti-curl means are evident from German Utility Model G 89 10 373.4.

Figure 2:
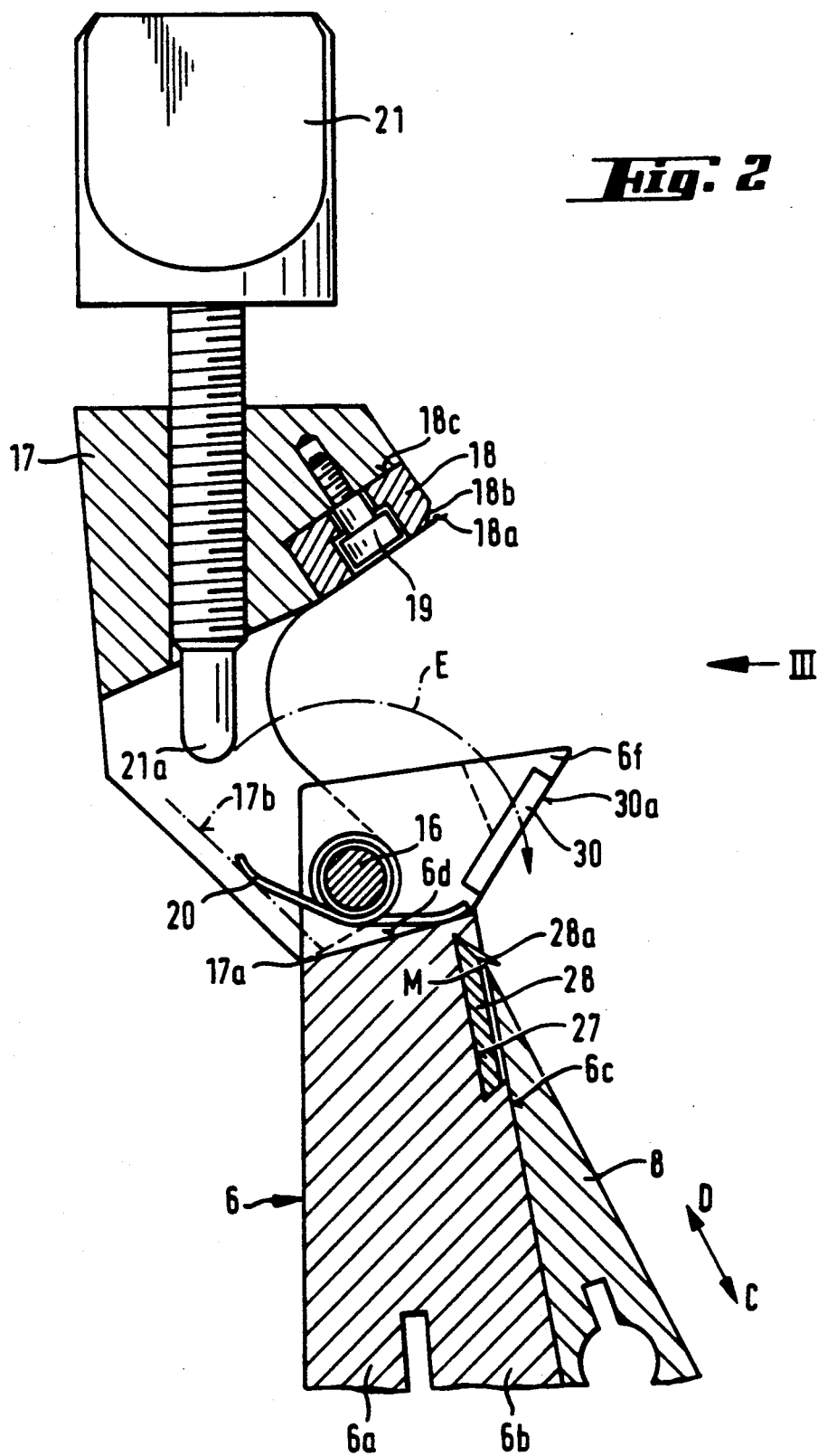
FIG. 2 shows a partial view of the clamping device according to FIG. 1 with the quick-action clamping means in opened position.
Figure 3:
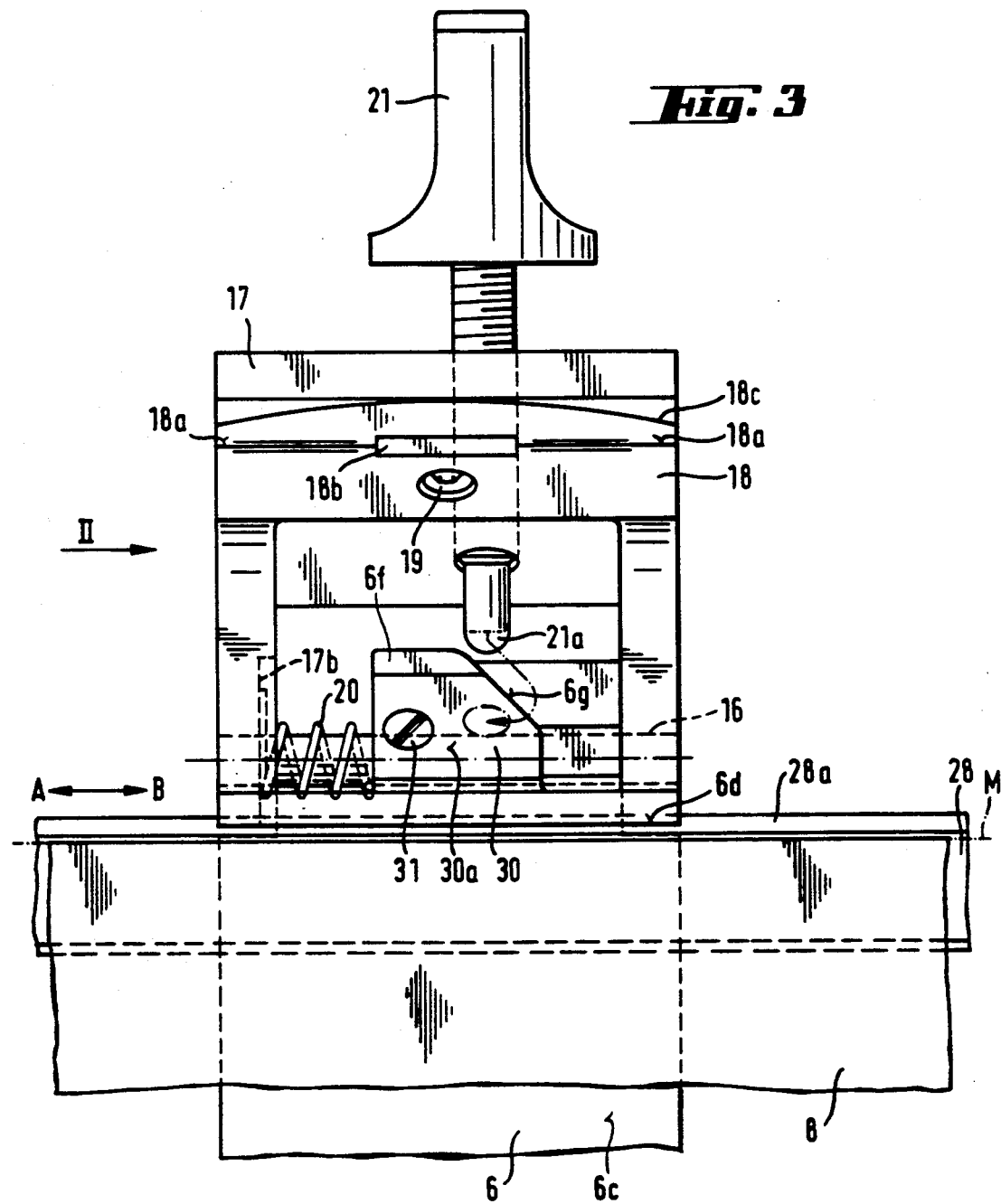
FIG. 3 shows a view of the quick-action clamping means in opened position along arrow III of FIG. 2.
Figure 4:
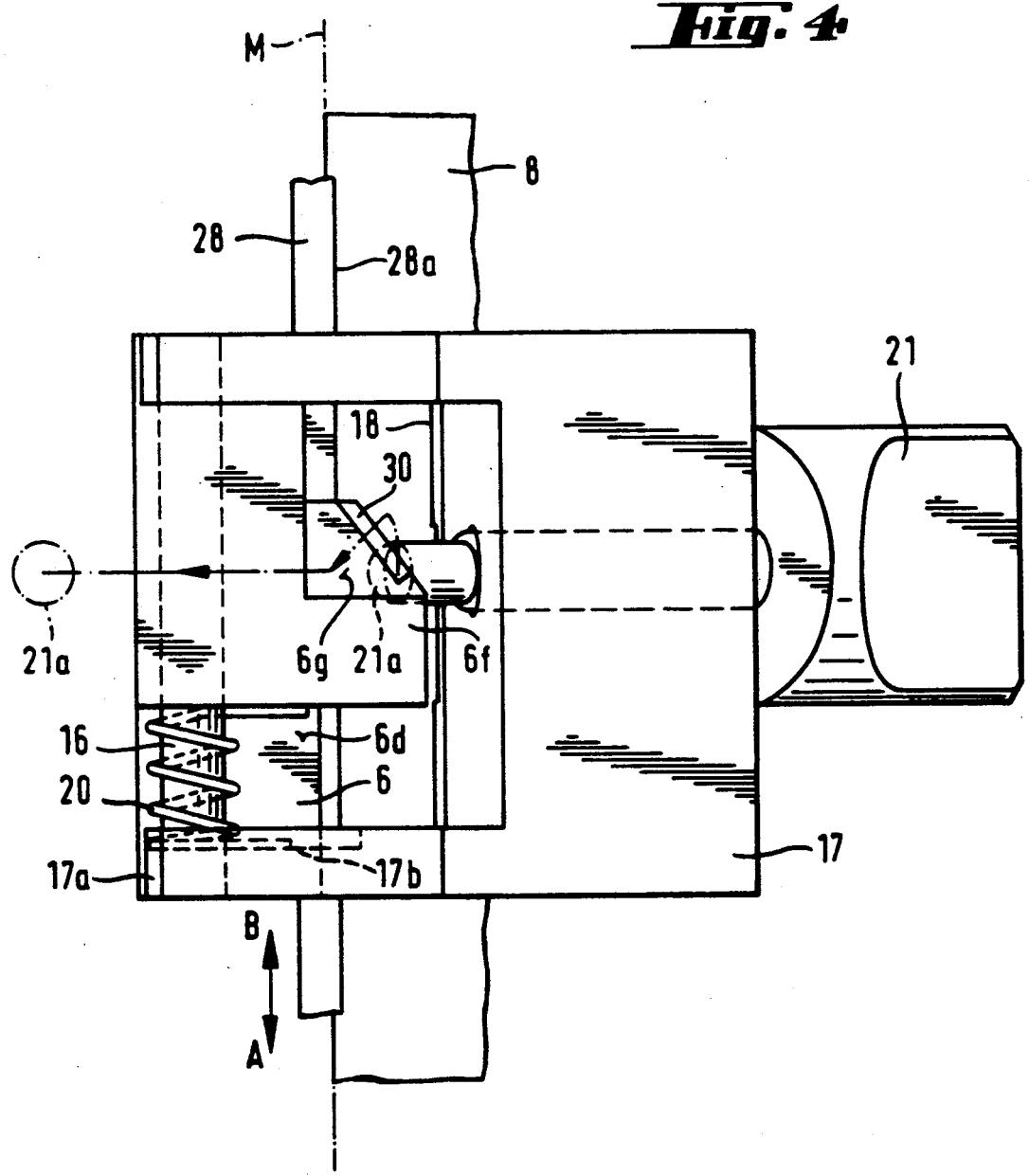
FIG. 4 shows a view of the quick-action clamping means in closed position along arrow IV of FIG. 1.

As is in particular evident from FIGS. 2 to 4, latch 17 is mounted on shaft 16 of jaw 6 for holding knife 8 in position tensioning screw 21 passes through latch 17. Tensioning screw 21 is supported with its end 21a on a bearing surface 30a of clamping jaw 6. Bearing surface 30a is provided by hardened platen 30 as protection against wear, its closed position, latch 17 rests with edge 18a floating member 18 extending parallel to the cutting edge of knife 8. Floating member 18 is pivotally connected to latch 17 by shoulder screw 19 which is loosely screwed into latch 17 such that it does not fully grip floating member 18 and contact surface 18c facing latch 17 is cambered so as to allow floating member 18 to perform pivotal movements about the point where it is screwed in. However, in order to ensure that edge 18a rests flush on the flank knife without being able to rock 18 edge 18a is formed with a central recess 18b (FIG. 3).

In its opened position, latch 17 rests with shoulder 17a on upper surface 6d of jaw 6 through the biasing action of spring 20 which is supported by shaft 16 of latch 17. One leg of spring 20 presses against upper surface 6d of jaw 6 and, the other leg presses against step 17b of latch 17.

In order to close latch 17, it is grasped by tensioning screw 21 and moved in the direction of arrow E until end 21a of the tension screw rests against support surface 30a. In order for screw end 21a to be able to move past projection 6f including platen 30 during this pivotal movement, the portion of jaw 6 is provided with a beveled face 6g which forces tension screw 21, and thus also latch 17 to shift on shaft 16 during the closing movement of latch 17 compressing spring 20 which is arranged on shaft 16 and, in its central portion, has a coil spring type configuration, towards the direction indicated by arrow B until screw end 21a can pass projection 6f.

Beveled face 6g is so designed that it releases screw end 21a as the pivotal movement approaches its end and thus allowing spring 20 to return latch 17 to its initial position. As a result, screw end 21a, as is apparent from FIG. 4 and others, can snap-in behind bearing surface 30a and exert a closing force on latch 17. By screwing down tension screw 21, knife 8 can be tightly held against jaw 6. This requires only a small rotational angle, because there is practically no backlash for tensioning screw 21.

In order to open latch 17, after the closing force of tensioning screw 21 has been released by a slight rotational movement—as is likewise evident from FIG. 4—it is merely required to slide latch 17 on shaft 16 compressing spring 20 in the direction indicated by arrow B so that latch 17 can swing into its opened position freely with tensioning screw 21 clearing projection 6f. In this open position, the clamping site for the knife is freely accessible from the front. This eliminates a troublesome insertion of knife 8 from the side or top which can easily result in a damaged knife edge. After knife 8 has been exchanged or laterally displaced to expose a new cutting edge, the quick-action clamping means of the invention can be closed again in easy fashion in that a slight pressure is exerted on the clamping latch in the direction indicated by arrow E.

According to FIG. 5, knife 8 is clamped against offset jaw 6 projects unsupported into cutting area. According to FIG. 6, two jaws 6 and 22 are provided, which each hold knife 8 on respective sides of the cutting area. Besides jaw 6, which in this case acts as main or principal jaw and therefore is located slightly closer to the cutting area, a supplementary jaw 22 is provided which is more remote to the cutting area. Since the cutting area is closer to main jaw 6, anti-roll plate 13 as offset by carrier means 15 to a position on shaft 14 laterally displaced from jaw 6 so that the cutting area remains freely accessible at least from the right-hand side.

Due to the modular construction of the microtome knife holder of the invention, it is possible to clamp the knife in two jaws which are approximately symmetrically arranged on either side of the cutting location—as shown in FIG. 6—which provides optimal stability.

As is evident from FIGS. 6 and 7, the supplementary clamping jaw 22 which may be narrower in dimension and thus less sturdy, includes a simpler means for clamping the knife. A narrow latch 24 is mounted for rotation on shaft 23. Unlike latch 17 of the main clamp, narrow latch 24 cannot slide on shaft 23. Knife 8 is tightened via tension screw 25 which rests on a bearing surface 22a. The actual pressure edge 26a is in this case, too, provided on floating member 26.

Finally, as is in particular evident from FIGS. 1, 2, 5 and 6, guards 28 are inserted in dovetailed recesses 27 in orienting surface 6c of the jaw 6 and like orienting surface of jaw 22 to prevent the cutting knife 8 from being touched. The upper edges of the guards ledge 28 are formed with lips 28a protruding beyond around the cutting edge of knife 8. Lips 28a prevent, on the one hand, the cutting knife from being accidentally touched and, on the other hand, from unintentionally tilting away from the orienting surface when the clamp is open. To facilitate adjustment of guards 28, grip 29 is provided at one end thereof to be grasped for manually exposing in whole or in part the cutting edge of knife 8. It is most desirable that the cutting edge be completely covered when not actually cutting specimens. When a single jaw and clamp are used, it is also recommended that the single guard be sufficiently long to cover the entire cutting edge.

What is claimed is:

1. A microtome knife holder for positioning a reusable type microtome knife comprising,
   a knife support, said support having an upwardly extending, knife orienting surface and a distal end,
   a knife clamping member, said member being pivotally mounted at one end thereof to said distal end, and
   means to force another end of said member toward said oriented surface for holding a knife,
   whereby a reusable type microtome knife can be mounted or removed from said holder in a direction normal to said orienting surface by pivoting said member away from said surface.

2. The microtome knife holder according to claim 1, further including a dovetailed recess extending across said orienting surface and a knife guard, said guard having a complimentary dovetailed portion adapted to slide in said recess and a guard portion extending from said dovetailed portion.

3. The microtome knife holder according to claim 1, further including a base and an adjustable support for carrying a butt end of a knife.

4. The microtome knife holder according to claim 2, further including an adjustable support for carrying a butt end of a knife.

5. The microtome knife holder according to claim 1, wherein said means comprises a bearing surface, said bearing surface being positioned at said distal end, and a pressure bolt extending through a threaded bore in said clamping member.

6. The microtome knife holder according to claim 2, wherein said means comprises a bearing surface, said bearing surface being positioned at said distal end, and a pressure bolt extending through a threaded bore in said clamping member.

7. The microtome knife holder according to claim 7, further including a spring, said spring urging said clamp member away from said orienting surface.

8. The microtome knife holder according to claim 7, further including an adjustable support for carrying a butt end of a knife.

9. A microtome knife holder for positioning a microtome knife comprising,
   a base, a dovetailed rail extending along an upper surface of said base, and a supporting member adapted to hold a microtome knife, said member having an upwardly extending, knife orienting surface and an elongated dovetailed recess extending parallel to said orienting surface, said dovetailed recess being adapted to slidably engage said rail for movement of said member parallel to said orienting surface, an elongated slot extending into said member from said dovetailed recess to provide first and second foot portions of said member and to make said dovetailed recess compressible, and means drawing said foot portions toward each other, whereby said supporting member is releasably fixed in a chosen position along said rail.

10. The microtome knife holder according to claim 9, wherein there is a further support member of like construction to said support member.

11. The microtome knife holder according to claim 9, further including a knife clamp, said clamp being pivotally mounted to said support for movement to a first position causing a knife to be forced against said orienting surface by said clamp and for movement to a second position away from said orienting surface said second position allowing a knife to be removed or placed in said holder by movement in a direction generally normal to said orienting surface.

12. The microtome knife holder according to claim 9, further including an adjustable support for carrying a butt end of a knife.

13. The microtome knife holder according to claim 11, further including an adjustable support for carrying a butt end of a knife.

14. A microtome knife holder having a knife guard comprising, a knife orienting surface, a dovetailed recess extending across said orienting surface and a knife guard, said guard having a complimentary dovetailed portion adapted to slide in said recesses and a guard portion extending from said dovetailed portion.

15. The microtome knife holder according to claim 14, wherein said dovetailed portion is contained within said recess.

16. The microtome knife holder according to claim 14, further including another orienting surface and guard of like construction.

17. The microtome knife holder according to claim 15, further including another orienting surface and guard of like construction.

* * * * *